United States Patent [19]

Gard et al.

[11] 4,158,778
[45] Jun. 19, 1979

[54] OPTOELECTRONIC SCANNING DEVICE

[75] Inventors: George E. Gard, Lancaster; Elvin K. Manning, Mountville; Werner Rueggeberg; Kerry L. Weinhold, both of Lancaster, all of Pa.

[73] Assignee: Armstrong Cork Company, Lancaster, Pa.

[21] Appl. No.: 882,327

[22] Filed: Mar. 1, 1978

[51] Int. Cl.² ............... G01N 21/38; G01N 23/00
[52] U.S. Cl. ........................... 250/461 R; 250/359
[58] Field of Search ........... 250/302, 358, 359, 360, 250/458, 461, 562, 563

[56] References Cited

U.S. PATENT DOCUMENTS

| 3,694,658 | 9/1972 | Watson et al. | 250/219 DF |
| 3,800,148 | 3/1974 | De Cock | 250/562 |
| 3,829,690 | 8/1974 | Snyder | 250/461 |
| 3,877,817 | 4/1975 | Ralston | 356/180 |
| 3,983,403 | 9/1976 | Dahlström et al. | 250/560 |

*Primary Examiner*—Alfred E. Smith
*Assistant Examiner*—Janice A. Howell

[57] ABSTRACT

An optoelectronic scanning device comprising two sets of photoresponsive elements adjusted to operate at different detection levels and aligned to scan materials marked with luminous paint and illuminated with ultraviolet light. The photo-elements are specially aligned to be optically responsive over an array of contiguous in-line domains and are coupled to trigger circuits to provide snap-action operation. The photo-elements and associated electrical components are heated and maintained at a constant temperature to ensure stable operation of the device.

4 Claims, 6 Drawing Figures

OPTOELECTRONIC SCANNING DEVICE

BACKGROUND OF THE INVENTION

The present invention relates generally to optical scanning devices and, more specifically, to optical scanning devices for detecting the position of inherent defects marked with luminous paint on wooden planks or boards.

Lumber for use in the manufacture of furniture must be free from defects such as checks, loose knots, or planar skips. Because of the high cost of clear boards of matched lengths, it has become customary to process boards containing imperfections to remove the defects and use the boards so processed to make glued-up stock. In the past, such processing of defective boards has entailed manually severing the boards to cut out the imperfect parts. These operations have been highly labor intensive, and as a result of their reliance on human judgment to determine how and where boards should be cut, the lumber has not always been processed with maximum efficiency.

Consequently, computer controlled sawing systems have been developed to process lumber to be used in the manufacture of glued-up stock. These operations normally involve several processing steps including visually inspecting the lumber and marking any defects with luminous paint, scanning the boards to detect and record the relative positions of the marked defects, automatically computing the most efficient way to cut the boards, and then ripping and cross-cutting the boards to remove the defects. A critical step in the development of computerized sawing operations has been the design of effective scanning units. These units must operate to register the position of a board and photoelectronically scan across the surface of the board to detect any marked defects. The device must be provided with sufficient sensitivity of response, accuracy of detection, speed of operation, and electrical stability so that the unit may operate reliably in service.

Accordingly, it is an object of the present invention to provide a photoelectric scanning device capable of reliably detecting luminous marks on lumber boards.

It is another object of the present invention to provide a photoelectric scanning device of adequate sensitivity to detect small luminous marks, of sufficient locational capability to accurately determine the position of small marks, and of sufficient speed of operation to allow the device to rapidly accomplish its functions.

It is a further object of the present invention to provide a photoelectric scanning device of adequate stability of electrical operation and of competent output for interfacing with an electronic computational unit, and to provide a scanning device otherwise well suited to the purposes for which the same is intended.

SUMMARY OF THE INVENTION

A photoelectronic device comprising an array of phototransistors disposed to scan across the surface of boards marked with luminous paint and illuminated with ultraviolet light. The phototransistors are mounted in two adjacent rows staggered with regard to one another, each row comprising a set of elements operating at a different detection level. The phototransistors are aligned by special optical and mechanical techniques to be optically responsive over a single array of contiguous collinear domains, alternate domains corresponding to phototransistors operating at different detection levels. The output of each phototransistor is coupled to a trigger circuit to provide snap-action operation. The phototransistors and associated electrical components are heated and maintained at a constant temperature to ensure stable electrical operation of the device.

DESCRIPTION OF THE PREFERRED EMBODIMENT

Figure 1:
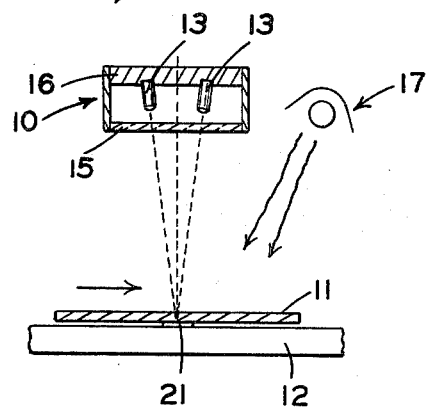
FIG. 1 is a transverse cross-sectional view of the scanner of the present invention, along with associated operational components.
Figure 3:
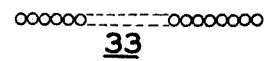
FIG. 3 is a diagram of the domains over which the photocells of the scanner of the present invention are intended to be responsive.
Figure 2:
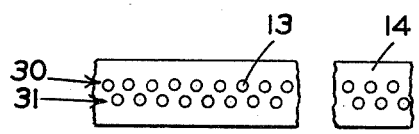
FIG. 2 is an underside view of the photocell array and mounting block of the scanner of the present invention.

Referring now to the drawings wherein like reference characters designate like or corresponding parts throughout the several views, FIG. 1 shows a scanner 10, according to the present invention, positioned adjacent to ultraviolet source 17 and positioned above platform 12 across which board 11 is conveyed during the operation of the device. Scanner 10 comprises photocells 13 mounted in block 14, heater 16, and pyrex outer plates 15. The photocells are highly responsive, fast operating devices with lensed optics that permit their use at distances between one to two inches above the surface being scanned, such as General Electric L14-F photodarlington transistors. Heater 16 may be a resistive element heating device such as a speedfoil heater, controlled by a proportional temperature controller. Block 14 is thermally insulated from the supporting structure and covered by pyrex-glass plates 15 to minimize temperature fluctuations. As illustrated in FIG. 2, the photocells 13 are mounted in block 14 in adjacent rows 30 and 31 staggered with respect to one another down the length of the block. Photocells in separate rows are chosen or adjusted to operate at different detection levels; row 30 may operate at a high detection level while row 31 operates at a low detection level. The photocells 13 are specially aligned to be responsive over an array of contiguous collinear domains 33, as illustrated in FIG. 3, on the surface of platform 12. Alternate domains 33 correspond to photocells from separate rows so that alternate domains operate at high or low detection levels depending on the row of photocells to which they correspond.

Figure 4:
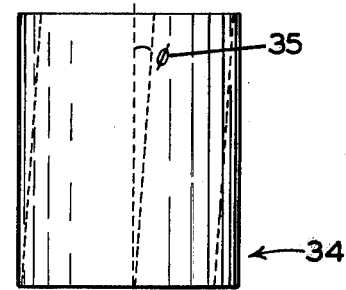
FIG. 4 is a cross-sectional view of a right angle corrective bushing used in the present invention to provide proper photocell alignment.

Photocells 13 are frequently subject to variations in manufacture which result in their optical axes not being aligned with their geometric axes. The optical alignment of the photocells so that they are responsive over the desired domains is accomplished by the devices shown in FIGS. 4 and 5. The geometric alignment of the photocells 13 in their mounting holes in block 14 may be altered by providing right cylindrical bushings 34 in the mounting holes and skewing the bushing an appropriate angle so that, when the photocell is fitted in the bushing, its optical axis will correspond to the geometric axis of mounting hole in the mounting block. The bushings would be skewed an angle φ 35, corresponding to the difference between the optical and geometric axes of the photocell. Alternatively, a corrective lens 36 may be substituted for the lens of a photocell whose optical and geometric axes are not in coincidence. Lens 36 has its optical center displaced a distance 37 so that the optical axis of the photocell is corrected to coincide with its geometric axis, and when the photocell is fitted in its mounting hole in block 14, it will be responsive over the proper domain area.

Figure 5:
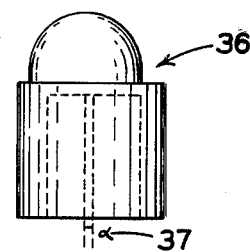
FIG. 5 is a cross-sectional view of a corrective lens used in the present invention to provide proper photocell optical alignment.
Figure 6:
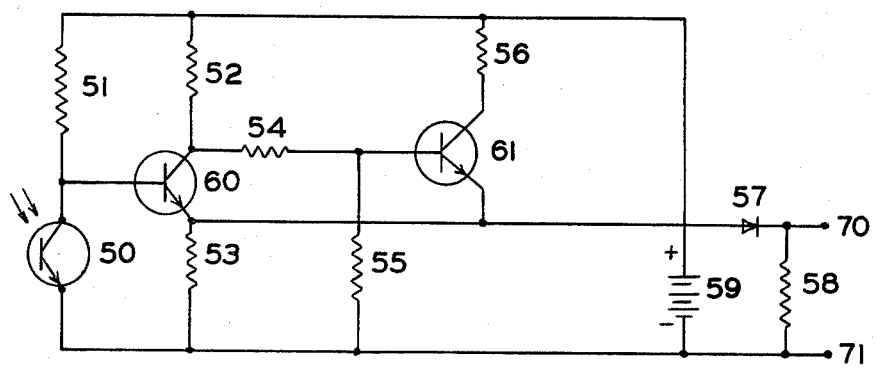
FIG. 6 is a diagram of the circuit used in the present invention to provide square wave output and snap-action operation.

In order to provide an output suitable as an input to electronic computing devices, the slow varying response generated by most phototransistors should be modified to become a square wave response having more positive and desirable registration characteristics. FIG. 5 illustrates a circuit which may be employed to produce square wave responses given slow varying inputs. Power supply 59, which may be any conventional 15 volt power supply, is used to energize the circuit and is suitably coupled across transistors 60 and 61 as well as phototransistor 50. The output of phototransistor 50 is connected across the emitter of transistor 60. Resistors 51, 52, and 53 are used to provide proper biasing, resistor 51 is matched to phototransistor 50 while resistors 52 and 53 may be 1000 ohms and 10 ohms respectively. The output of transistor 60 is in turn connected across the emitter of transistor 61. Resistors 52, 54, 55, 56, and 53 are used to provide proper biasing, resistors 54, 55, and 56 may be 270 ohms, 1000 ohms, and 200 ohms respectively. The emitter of transistor 61 is coupled across resistor 58 through diode 57 to provide output across terminals 70 and 71. Transistors 60 and 61 may be Motorola Bipolar NPN 40234 transistors. In operation, a slow varying pulse type drop in voltage across the phototransistor 50 results in a cessation of current flow through transistor 60. When current flow through transistor 60 is shut-off, the resistor network 52, 54 and 55 provides immediate forward bias to the emitter junction of transistor 61 which, in turn, causes transistor 61 to be switched-on. When the transistor 61 is switched on, a path for current flow is provided through resistor 56, transistor 61, diode 57, and resistors 53 and 58. When the voltage across phototransistor 50 rises at the end of an input pulse, transistor 60 turns on, immediately shutting off transistor 61 by processes corresponding to those described above for the case of a voltage drop across the phototransistor. The variations in voltage drops across parallel resistors 53 and 58 as the current flow is rapidly switched from through transistor 60 to through transistor 61 and back again provides a sharp square wave output pulse across terminals 70 and 71. Diode 57 insures that no current drop at all is run across terminals 70 and 71 until at least approximately 0.6 volts drop is provided across resistor 53.

Now with reference to FIG. 1, in overall operation, boards 11 are conveyed across platform 12. As the boards 11 are so conveyed phototransistors 13 scan the upper surface of the boards across their width and along their length as they move. Ultraviolet lamp 17 stimulates any luminous marks, such as chalk, ink, or paint, to fluoresce emitting light compatible with the spectral sensitivities of the phototransistors 13. Ultraviolet exactation of 2500 microwatts per square centimeter at 3660 Angstrom is most satisfactory. Board speeds past the scanner 10 of 150 feet per minute up to 300 feet per minute are most preferred. Fluorescent tape 21 on the top surface of platform 12 fluoresces when board 11 is not in place and along each side of the board and before and after each board as the board passes under the scanner. Thereby, the width and length of the board are determined as well as the relative location of any luminous marks, indicating defects, on the boards as it passes under the scanner 10. Luminous marks on the board are read as square wave pulses at the output of the scanner 10 from the trigger circuits previously described. Alternate photocells 13 trigger at low detection levels to provide good definition of narrow or lightly made marks. Phototransistor sensitivity variation incurred through ambient temperature changes is eliminated through heating of block 14 by heater 16 to a standard, such as 145° F., thermostatically controlled temperature, at which temperature the response sensitivity of the phototransistors is also substantially improved.

Since many changes could be made in the above construction and many apparently widely different embodiments of this invention could be made without departing from the scope thereof, it is intended that all matter contained in the above description or shown in the accompanying drawings shall be interpreted as illustrative and not in a limiting sense.

What is claimed is:

1. A photoelectric scanning system for detecting luminous marks on boards conveyed past the components of the system, comprising:
    (a) a first row of phototransistors aligned to be responsive over a collinear array of equally spaced domains;
    (b) a second row of phototransistors mounted adjacent to and alongside said first row of phototransistors, said second row of phototransistors adjusted to operate at a lower detection level than said first row of phototransistors and aligned to be responsive over a collinear array of equally spaced domains disposed between and contiguous with the domains over which said first row are responsive, thereby providing that alternate domains are responsive at different detection levels;
    (c) an ultraviolet lamp for illuminating materials to be scanned by said phototransistors;
    (d) a heater including a temperature controller mounted on said phototransistor array for maintaining said array at a constant elevated temperature; and
    (e) a trigger circuit having transistor components for correcting the output of said phototransistors into square wave output.

2. The system of claim 1, further including skewed right angle bushings into which said phototransistors are mounted to correct their optical alignments.

3. The system of claim 1, wherein said second row of phototransistors is mounted staggered with respect to said first row of phototransistors.

4. The system of claim 1, further including fluorescent tape mounted on the plane of the materials to be scanned by said phototransistors for indicating the limits of positions of said materials.

* * * * *